United States Patent [19]

Lawniczak et al.

[11] Patent Number: 5,000,561
[45] Date of Patent: Mar. 19, 1991

[54] CONTROL ARRANGEMENT FOR AN APPARATUS FOR OPHTHALMOLOGICAL TREATMENT

[75] Inventors: Michel Lawniczak, Steffisburg; Paul Bätscher, Munsingen; Robert Meerstetter, Thun, all of Switzerland

[73] Assignee: Lasag AG, Thun, Switzerland

[21] Appl. No.: 417,574

[22] Filed: Oct. 5, 1989

[30] Foreign Application Priority Data

Oct. 6, 1988 [CH] Switzerland ............... 03744/88

[51] Int. Cl.⁵ ............................ A61B 3/10; A61B 17/36
[52] U.S. Cl. ........................................ 351/221; 606/4
[58] Field of Search ................... 351/214, 221, 245; 74/471 XY, 471 R; 606/4, 5, 6

[56] References Cited

U.S. PATENT DOCUMENTS

| | | | |
|---|---|---|---|
| 4,470,320 | 9/1984 | Kim | 74/471 |
| 4,554,917 | 11/1985 | Tagnon | 128/303.1 |
| 4,736,744 | 4/1988 | Koike et al. | 606/4 |

FOREIGN PATENT DOCUMENTS 3601022 7/1987 Fed. Rep. of Germany .
2154306 9/1985 United Kingdom .

Primary Examiner—Paul M. Dzierzynski
Attorney, Agent, or Firm—Griffin Branigan & Butler

[57] ABSTRACT

The control arrangement (13) of this invention includes a casing on which the hand (22) of a medical practitioner may rest when the position of the point of focus of a laser beam onto a place to be surgically treated is sought. The arrangement includes a roller (20) operated by the thumb (21) and a ball (23) operated by the index finger (24), the roller and the ball respectively displacing the point of focus along a first coordinate axis (Z) and along second and third coordinate axes (X Y). A push button (25) operated by the middle finger (26) controls firing of the laser beam. The arrangement is used in ophthalmology.

11 Claims, 3 Drawing Sheets

CONTROL ARRANGEMENT FOR AN APPARATUS FOR OPHTHALMOLOGICAL TREATMENT

This invention concerns an arrangement for controlling an apparatus for ophthalmological treatment, said apparatus including at least one laser power beam having a focal point of concentration of said beam capable of acting when fired by a practitioner on a predetermined location within the eye of a patient, said location being defined by first, second and third dimensional orthogonal coordinates.

BACKGROUND OF THE INVENTION

An apparatus for ophthalmological treatment for which it is necessary to assure control is described for instance in the European patent document EP-B-0 030 210. The apparatus includes essentially a first light source which emits a laser power beam intended for treatment, and a second light source which emits a visible coherent light beam of low power arranged to envelop the power beam. Such beams then pass through a converging lens which concentrates them at a focal point, this being the point of treatment, the visible light beam being present in order to permit localization with precision of the place where the point of focus of the power beam is to be found. The point of focus is observed by a medical practitioner through an eye piece (or binocular) while the ocular cavity is illuminated by an auxiliary source of light. When the place sought for treatment is reached, the practitioner may fire the power beam.

Apparatus of the prior art may appear more or less as shown on FIG. 1. The treatment apparatus includes a table 1 in front of which a practitioner 2 may be seated. On the other side of the table will be found a patient 3, here recumbent on a bed 4 which is precision recessed into the table. In certain cases the patient is seated and rests his head on a chin rest fastened to the table. Whatever be the position chosen for the patient, the apparatus is conceived in order that the head of the patient be immobilized relative to the said apparatus.

FIG. 1 further shows a cabinet 5 supporting the table. This support generally contains sources giving rise to the power beam and the visible light beam as mentioned hereinbefore. These beams are led to the interior of the eye of the patient by a column 6 and a movable arm 7, this latter bearing an output optical system 8 adapted to focus the beams down to a point which must be brought to a precisely determined place within the eye of the patient, such point being observed by the practitioner through the binocular 9. To this end arm 7 may be displaced according to three orthogonal coordinate axes X, Y and Z.

In order to displace the beams coming out of the optical system 8 and to direct them to a precise point within the ocular cavity, the practitioner employs a contact lens 10 which is held on the eye of the patient. In this case his left hand 11 is occupied. The right hand 12 of the practitioner must thus be capable of alone operating the control arrangement 13 which is not described in the document cited hereinabove and which must permit control of at least four functions: that of displacement of the column 7 according to three coordinates X, Y and Z and that of firing the laser at the moment when the three coordinates which have been sought are attained. It can be readily imagined without any particular inventive activity that the control arrangement 13 includes four distinct elements controlling respectively the displacements X, Y and Z of the laser beam, the first three elements being rollers which may be operated in both senses and the fourth element being a simple push-button. Such an arrangement is awkward since it obliges the practitioner to memorize the location of the rollers and the functions which are attached to them with risks of error or loss of time that such a system may cause, since the eyesight of the practitioner is entirely occupied in observing the eye cavity to be cared for and must not be distracted to check for instance if the correct control element has been operated.

SUMMARY OF THE INVENTION

Thus, in order to avoid the difficulties listed hereinabove, this invention is characterized in that the control arrangement comprises a casing on which may rest a hand of a practitioner, said casing being provided with first means for fixing a focal point according to the first coordinate, a second means for fixing the focal point in a plane according to second and third coordinates and third means for releasing the laser beam when said three coordinates have been attained, said first, second and third means being arranged in a manner such that they may each be controlled by the fingers of the same hand.

The invention will now be explained having reference to the attached drawings which illustrate it by way of example.

DESCRIPTION OF THE PREFERRED EMBODIMENT

Figure 1:
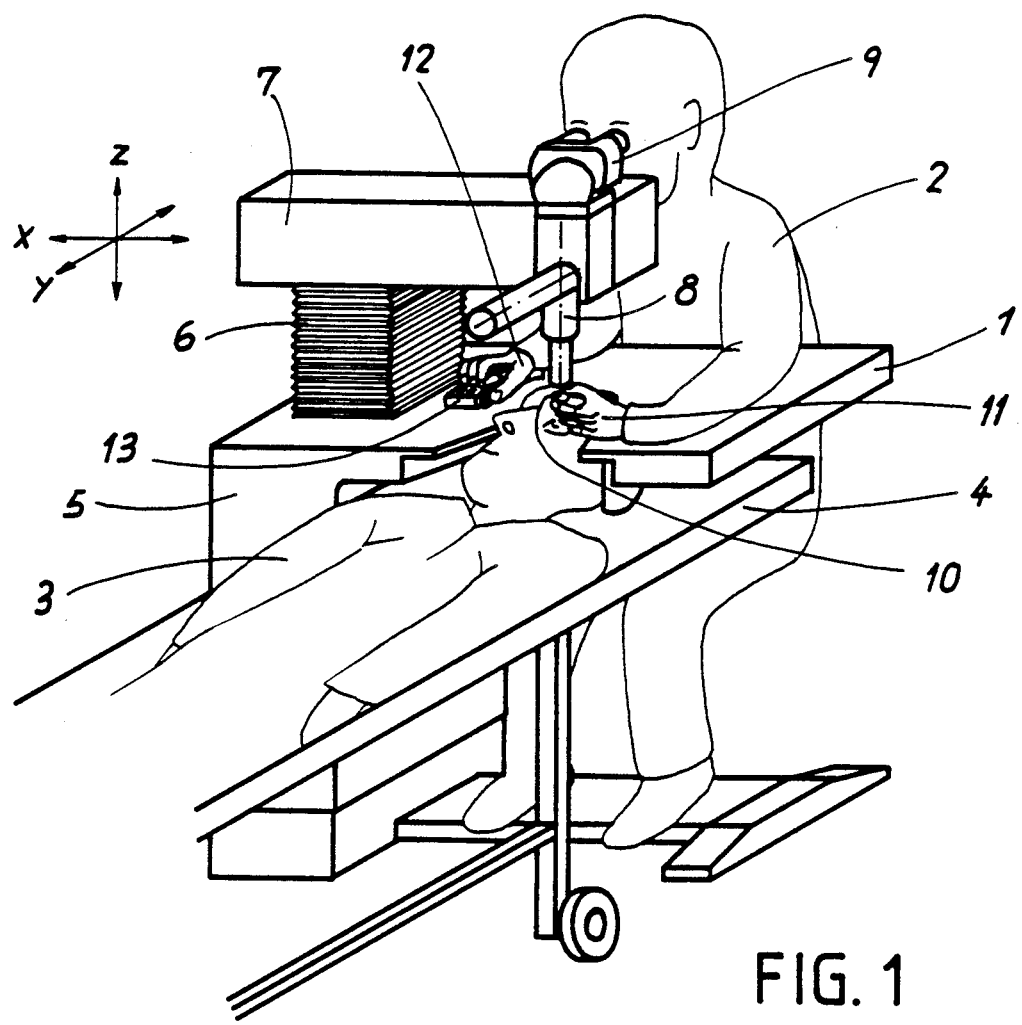
FIG. 1 shows in perspective an apparatus for ophthalmological treatment which employs a control arrangement in accordance with the invention.

The ophthalmological treatment apparatus of FIG. 1 has been described hereinabove as forming part of the state of the art. This apparatus is controlled by means of an original apparatus 13 which will be described in referring to FIGS. 2, 3 and 4.

Figure 2:
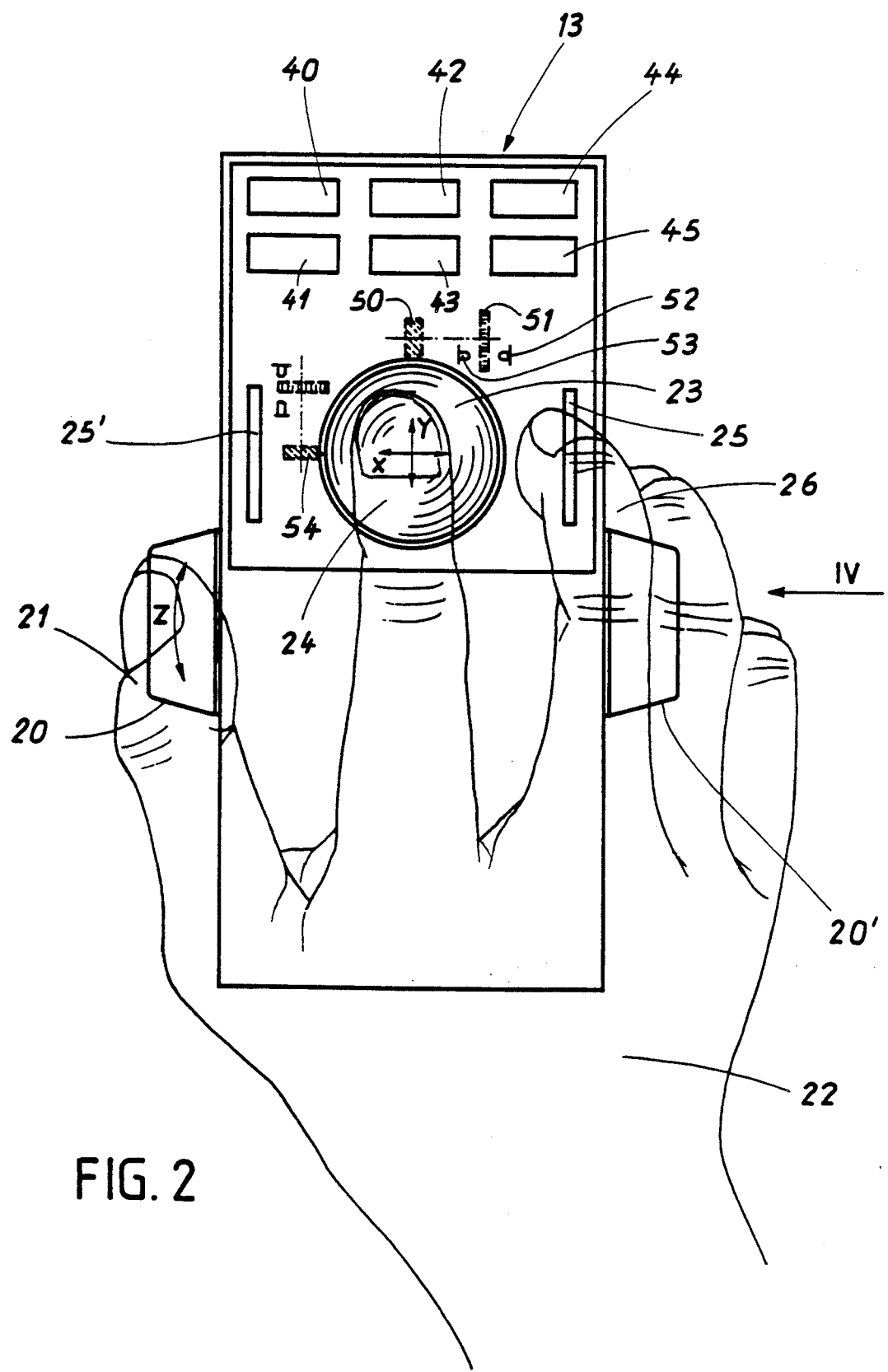
FIG. 2 is a view from above of the control arrangement according to the invention here being operated by the right hand of a right-handed practitioner.

As may be seen on FIG. 2, the arrangement 13 is a casing on which has been shown a hand of a practitioner. The arrangement is provided with a first means for fixing the focal point of the laser beam according to a first coordinate. The figure shows that this first means is here a roller 20 which may be rotated by a first finger 21, here the thumb of the right hand 22. FIG. 2 further shows that the arrangement is provided with a second means for fixing the focal point of the laser beam in a plane according to the second and third coordinates. This second means here is a ball 23 adapted to be rolled by a second finger 24, here the index finger of the right hand 22. Finally, FIG. 2 shows that the arrangement includes a third means for firing the laser beam as soon as the three coordinates have been attained by the operation of the first and second means. This third means here is in the form of a push-button 25 adapted to be operated by a third finger 26, in this case the middle finger of the right hand 22. In a completely general manner, one notes that the first, second and third means are arranged in a manner such that they may be each controlled by a different finger of the same hand.

It may be observed that the arrangement uses only two fingers in order to bring the focal point of the beam to the desired place, and this thanks to the employment of a single means (the ball) for positioning the focal point within a plane. The use of the index finger to assure the seeking out of two coordinates in a plane is particularly advantageous because on the one hand of the excellent mobility which this finger has in comparison with the mobility of the other fingers and on the other hand the ability of independent action of this finger relative to the others. The employment of the thumb for the searching out of a single coordinate is here judicious, this finger being less mobile but lending itself well t the action in rotation which one requires in order to operate the roller. Finally, the employment of the middle finger for releasing the laser beam is advantageous above all because of its position well adapted to operate a push-button.

If one should attribute to the first coordinate the determination of a focal point relative to the depth of the eye and to the second and third coordinates, the fixation of a focal point in a plane parallel to the face of the patient, one will have furthermore a logical sequence of actions undertaken initially by the thumb, then by the index and finally by the middle finger when the two first fingers are fixed in a position for which the firing may take place, this logical sequence corresponding to the logical rank which the thumb, index and middle finger of one hand occupy.

Figure 3:
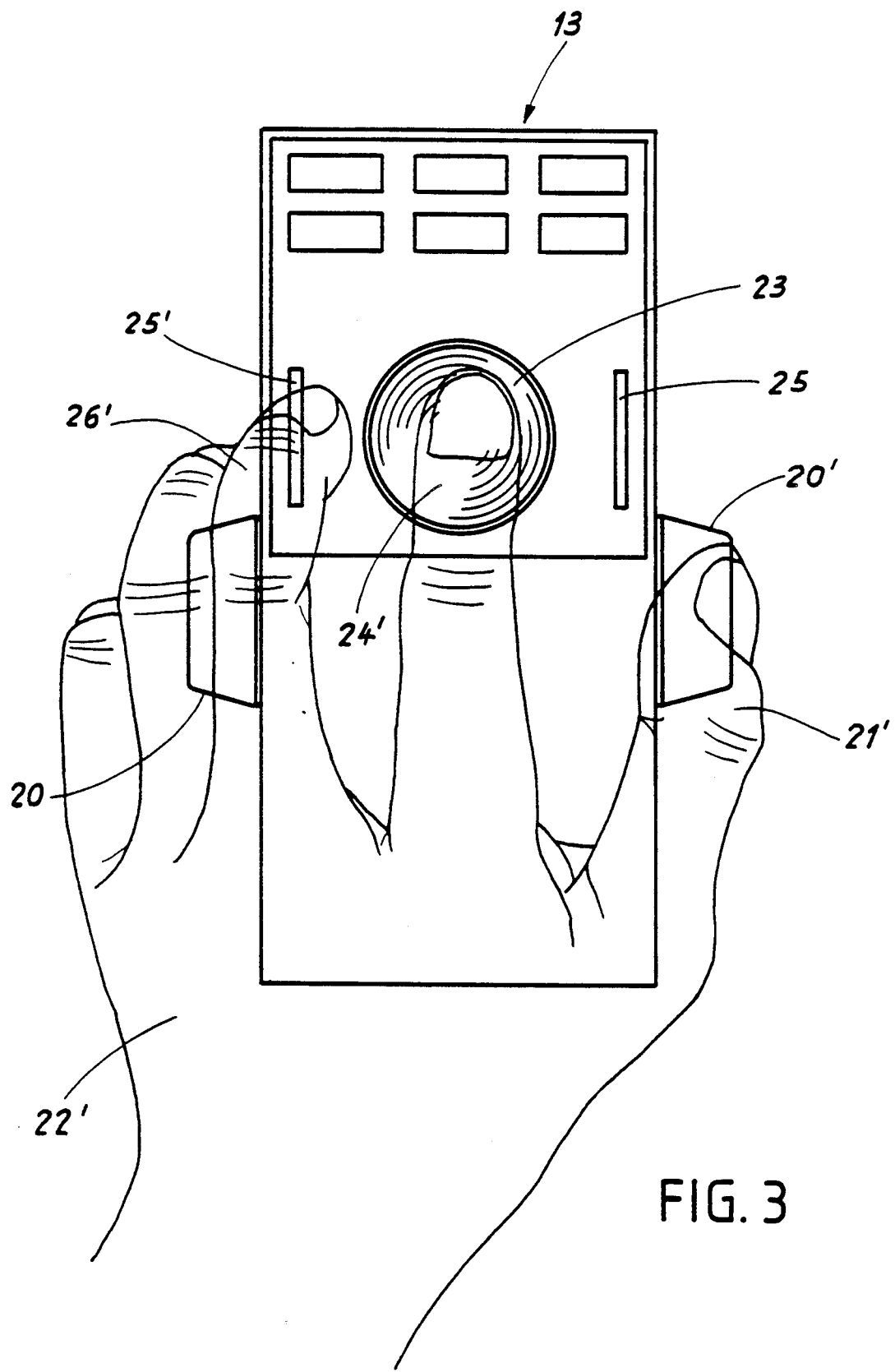
FIG. 3 is a view from above of the control arrangement in accordance with the invention, here operated by the left hand of a left-handed practitioner.

FIG. 2 shows that the roller 20 and the push- 0 button 25 are duplicated by a second roller 20' and a second push-button 25'. This arrangement enables utilization of the control arrangement likewise by the left hand as has been shown on FIG. 3. In FIG. 3 the left hand 22' by its thumb 21', index 24' and middle finger 26' controls respectively roller 20', ball 23 and push-button 25'. On FIG. 3 will be found the same advantageous arrangement of controls, set out likewise in a completely logical manner, but this time for use by the left hand.

If one should now refer to FIG. 4, which is a view along arrow IV of FIG. 2, there will be found on arrangement 13 the same three control means which have been described hereinabove, i.e. in order roller 20', ball 23 and push-button 25. This view shows furthermore an additional particularity of the invention which consists in breaking the face against which the hand is supported into a first rising zone 30 adapted to serve as wrist support for the hand and a second falling zone 31 on which are placed the ball 23 and the push-buttons 25, 25' controlled respectively by the index and the middle finger of the hand (not shown here). This arrangement having a broken face is well adapted to support the hand and contributes, if one adds the careful arrangement of the controls themselves, to an ergonomic arrangement particularly well chosen which facilitates rapid action without error and reduces both physical and mental fatigue of the practitioner.

Figure 4:
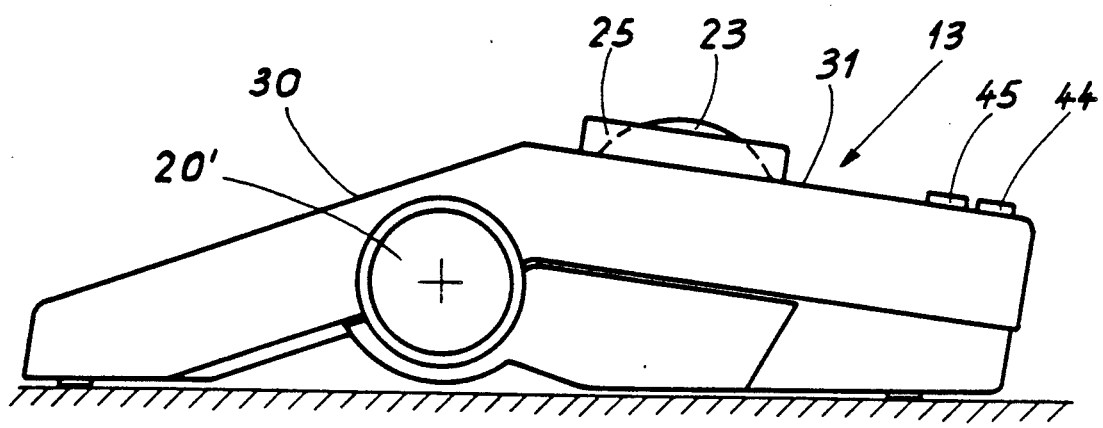
FIG. 4 is a lateral view of the arrangement according to the invention and according to arrow IV of FIG. 2.

FIGS. 2, 3 and 4 show that the control arrangement may further include fourth means for rapidly reaching a zone located within the surroundings close to the place where the laser firing must take place. It comprises in fact push-buttons enabling a coarse pre-adjustment according to the three coordinates. In these figures push-buttons 40 and 41 enable a rapid search for the first coordinate. It is likewise for push-buttons 42, 43 and 44, 45 which enable the same rapid search but for the second and third coordinates respectively.

The means for displacing the focal point within a plane by means of a single finger here consists in employing a ball which may roll freely about its center. One could also envisage other means, for instance the employment of the device commonly known as the joystick in place of the ball. The employment of a joystick however leads to problems of stability of the position and of precision.

FIG. 2 shows that the ball has been assigned coordinates X and Y. In a general manner known in the state of the art, ball 23 drives two wheels 50, 54 orthogonally arranged relative to one another. The figure shows that wheel 50 drives a disc 51. Such disc is pierced with slots which allow passage of the light emitted by a lamp 52. On the other side of the disc is found a photoelectric sensor which receives the light traversing the slots. The electrical pulses issuing from the sensor control a power electronic device which in its turn controls for instance a stepping motor. Such motor controls the arm 7 of the ophthalmological apparatus shown on figure 1 and this according to coordinate Y. A similar arrangement is provided for displacement of the arm in accordance with coordinate X from wheel 54. Coordinate Z is controlled by the thumb 21 acting on roller 20. The angle of rotation of the roller may also be converted into electrical pulses as explained hereinabove.

The ball system adapted to displace a point within a plane, is known today and is employed for instance in certain personal computers. In this application the system is inverted relative to that described here, i.e. it is not a finger which displaces the ball, but the hand which causes the case to move over a table, the ball being found under the casing and rolling when one displaces the casing. This arrangement is commonly known as a mouse and is described in particular in the review "Mini & Micros" Nr. 305, 22 June 1988. Here one finds an embodiment under the registered trademark "Logimouse" marketed by Logitech S.A. CH-1143 Apples, Switzerland. The mouse system, however, has the inconvenient feature of requiring much space for moving the casing around the table and becomes rapidly dirty. Furthermore, it is readily seen that it is more difficult to immobilize the entire hand than a single finger of this hand when the position of the focal point has been found. Above all, if another finger must further control a roller (coordinate Z), it may be added that the system proposed in this invention enables rapid attainment of the point sought for and this with high precision and less effort.

The ball 23 here described is employed for displacing the focal point in a plane XY. One may however consider that it could likewise serve to displace this point in accordance with coordinate Z. This additional function may readily be fulfilled should one add to the ball a possibility of being pushed in so as to act on a contact itself setting into operation a motor for driving the arm according to coordinate Z. Under these conditions, a single finger of the hand is sufficient to control the arm in the three directions, the index 24, 24' for instance. Likewise under these conditions the firing function may be fulfilled either by the thumb 21, 21' or by the middle finger 26, 26'.

The description which has just been given is based on an apparatus for treatment of a recumbent patient. The displacement controlled by the ball is then in a plane perpendicular to the vertical. If the patient should be seated, it will be understood that the displacement controlled by the ball will have to be made in a plane parallel to the vertical. For this, the control arrangement will be provided if necessary with a system for permuting the coordinates.

We claim:

1. A control arrangement for an apparatus for ophthalmological treatment, said apparatus including at least one laser power beam having a focal point of concentration of said beam capable of acting when fired by a practitioner on a predetermined location within the eye of a patient, said location being defined by first, second and third dimensional orthogonal coordinates, said control arrangement comprising a casing on which a hand of a practitioner may rest, said casing being provided with a first means for fixing the focal point according to the first coordinate, a second means for fixing the focal point within a plane according to the second and third coordinates and a third means for releasing the laser beam when said three coordinates are reached, said first, second and third means being arranged in a manner such they may each be controlled by the fingers of the same hand, said first and second means comprising a ball adapted to be respectively pressed in and rolled by a first finger and the third means comprising a push button adapted to be pressed in by a second finger.

2. A control arrangement as set forth in claim 1 further comprising fourth means permitting a coarse preadjustment in order to lead said focal point in a zone within the surroundings close to the location where release of the laser beam is to take place.

3. A control arrangement as set forth in claim 1 wherein the first, second and third means are arranged in a manner such that they may be controlled respectively by the index finger and the thumb or the middle finger of the hand of the practitioner.

4. A control arrangement as set forth in claim 1 wherein said first and second means are arranged in a manner such that they may be indifferently controlled by the right hand or the left hand of the practitioner such control being effected respectively by the thumb, the index finger and the middle finger of one or the other hand.

5. A control arrangement as set forth in claim 4 wherein the casing has the form of a parallelepiped which on the face on which the hand may rest exhibits a ball which may be rolled by the index finger of the hand in order to fix the second and third coordinates and two push buttons located on either side of the ball so as to control firing of the laser beam by the middle finger of the hand, said casing exhibiting on each of its lateral faces a roller adapted to be rotated by the thumb of the hand in order to fix the first coordinate.

6. A control arrangement as set forth in claim 5 wherein said face is broken and exhibits a first rising zone adapted to serve as a wrist support for the hand and a second falling zone on which are arranged the ball and the two push buttons.

7. A control arrangement as claimed in claim 1 wherein said first and second means accomplish a fine adjustment of said focal point, said arrangement further comprising fourth means operating rapidly as compared to said first and second means for coarsely fixing said focal point prior to fine adjustment thereof.

8. A control arrangement for an apparatus for ophthalmological treatment, said apparatus including at least one laser power beam having a focal point of concentration of said beam capable of acting when fired by a practitioner on a predetermined location within the eye of a patient, said location being defined by first, second and third dimensional orthogonal coordinates, said control arrangement comprising a casing on which one hand of a practitioner may rest, said casing being provided with a first means for fixing the focal point according to the first coordinate, a second means for fixing the focal point within a plane according to the second and third coordinates and a third means for releasing the laser beam when said three coordinates are reached, said first, second and third means being arranged in a manner such they may each be controlled by the fingers of the same hand, said first means comprising a roller adapted to be rotated by a first finger, said second means comprising a ball adapted to be rolled by a second finger and said third means comprising a push button adapted to be pushed in by a third finger.

9. A control arrangement as set forth in claim 8 wherein said first, second and third means are arranged in a manner such that they may be controlled respectively by the thumb, the index finger and the middle finger of the hand of the practitioner.

10. A control arrangement for an apparatus for ophthalmological treatment, said apparatus including at least one laser power beam having a focal point of concentration of said beam capable of acting when fired by a practitioner on a predetermined location within the eye of a patient, said location being defined by first, second and third dimensional orthogonal coordinates, said control arrangement comprising a casing on which one hand of a practitioner may rest, said casing being provided with a first means for fixing the focal point according to the first coordinate, a second means for fixing the focal point within a plane according to the second and third coordinates and a third means for releasing the laser beam when said three coordinates are reached, said first, second and third means being positioned on said casing so that they may be controlled by and simultaneously contacted by the fingers of said one hand when said one hand is resting on said casing.

11. A control arrangement as claimed in claim 10 wherein said first, second and third means are positioned on said casing so that they may be simultaneously contacted by the thumb, index finger and middle finger, respectively, of said one hand when said one hand is resting on said casing, or the other hand of the practitioner when said other hand is resting on said casing.

* * * * *